United States Patent [19]

Grice

[11] Patent Number: 4,895,820

[45] Date of Patent: Jan. 23, 1990

[54] CATALYTIC PROCESS FOR THE PREPARATION OF LINEAR POLYETHYLENEPOLYAMINES USING A TITANIA-SUPPORTED PHOSPHAMINE CATALYST FOR THE PREPARATION OF LINEAR POLYETHYLENE POLYAMINES

[75] Inventor: Neal J. Grice, Austin, Tex.

[73] Assignee: Texaco Chemical Company, White Plains, N.Y.

[21] Appl. No.: 139,556

[22] Filed: Dec. 30, 1987

[51] Int. Cl.$^4$ .................... B01J 27/10; B01J 27/135; B01J 27/14; B01J 27/24

[52] U.S. Cl. .................................... 502/200; 502/208

[58] Field of Search ............................... 502/208, 200

[56] References Cited

U.S. PATENT DOCUMENTS 4,584,406  4/1986  Vanderpool et al. ............... 564/479

Primary Examiner—W. J. Shine
Attorney, Agent, or Firm—Jack H. Park; Kenneth R. Priem; Carl G. Ries

[57] ABSTRACT

Novel catalysts are disclosed which are prepared by reacting a minor amount of phosphonitrillic chloride with titania to form an intermediate reaction product that is reacted with a diamine chelating agent to provide a catalyst that can be used effectively to catalyze the reaction of monoethanolamine with ethylenediamine.

15 Claims, 1 Drawing Sheet

CATALYTIC PROCESS FOR THE PREPARATION OF LINEAR POLYETHYLENEPOLYAMINES USING A TITANIA-SUPPORTED PHOSPHAMINE CATALYST FOR THE PREPARATION OF LINEAR POLYETHYLENE POLYAMINES

BACKGROUND OF THE INVENTION

1. Technical Field of the Invention

This invention relates to a process for the preparation of predominantly linear polyethylenepolyamines from ethylenediamine and monoethanolamine in the presence of unique catalyst compositions prepared from the reaction product of a minor amount of phosphonitrillic acid with titania.

2. Prior Art

Heretofore, polyethylenepolyamine compounds such as diethylenetriamine, triethylenetetramine and the higher homologs have been produced by the reaction of an alkyl halide such as ethylene dichloride with an amine such as ammonia or ethylenediamine at elevated temperatures and pressures. Normally, relatively high yields of predominantly non-cyclic polyethylenepolyamine compounds are obtained from this process with varying yields of heterocyclic amines. The large amounts of energy required to produce the reactants as well as the difficult separation procedures required to recover the more valuable linear polyethylenepolyamines diminish the usefulness of the ethylene dichloride process. The hydrohalide salts of ammonia and the polyethylenepolyamine products must also undergo difficult and time consuming caustic neutralization to yield the free polyethylenepolyamines.

It has heretofore been known that phosphates can be used to catalyze reactions to produce predominantly heterocyclic rather than linear products. Thus, U.S. Pat. No. 3,297,701 teaches the use of aluminum phosphate to catalyze the reaction of ethanolamines and polyethylenepolyamines to yield cyclic compounds. U.S. Pat. No. 3,342,820 discloses the use of aluminum phosphate for the preparation of heterocyclic compounds such as triethylenediamine. As another example, U.S. Pat. No. 4,103,087 also discloses the use of aluminum phosphate catalysts for producing heterocyclic product compounds.

More recently, investigators have found that more linear products can also be obtained in a catalyst conversion. Johnson et al. U.S. Pat. No. 4,463,193 and U.S. Pat. No. 4,578,517 are directed to the reaction of an alkanolamine with an alkyleneamine and ammonia in the presence of a catalytically effective amount of a group IIIB metal acid phosphate to give primarily non-cyclic polyalkylene polyamine products. Thus, in Table 4 of U.S. Pat. No. 4,463,193, Johnson et al. disclose the reaction of monoethanolamine with ethylenediamine and ammonia using catalysts such as lanthanum acid phosphate and praseodynium acid phosphate at conversions of about 11 to 43% of monoethanolamine to give a noncyclic selectivity of about 67% to 92%. In Ford et al. U.S. Pat. No. 4,503,253, phosphoric acid incorporated onto an inert support (silica) was used as a catalyst and in Table 1 of the patent, use of this type of catalyst was shown to provide monoethanolamine conversions of 34% to 68% with a selectivity to noncyclics of 62% to 86%.

European patent application No. 0,073,520 dated August 31, 1982 for Ford and Johnson disclosed that the reaction of monoethanolamine with ethylenediamine and ammonia can be catalyzed with acidic metal phosphates, phosphoric or phosphorous acid or their anhydrides and alkyl or aryl esters (e.g., boron phosphate, ferric phosphate, aluminum phosphate, etc.). U.S. Pat. No. 4,314,083 discloses the reaction of ethylenediamine with monoethanolamine to prepare noncyclic polyalkylenepolyamines using, as a catalyst, a salt of a nitrogen or sulfur-containing compound.

In inventions originating in our laboratories, Brennan et al. in U.S. Pat. No. 4,036,881 discloses the use of phosphorus-containing catalysts to catalyze the reaction of ethylenediamine with monoethanolamine. Excellent results were obtained when the reaction was conducted in an autoclave. However, when the phosphorus compound was supported on silica or diatomaceous earth, good results were obtained only at comparatively low conversions. Brennan et al. U.S. Pat. No. 4,044,053 is also relevant in this regard. Brennan U.S. Pat. No. 4,448,997 is directed to an alumina phosphate-type catalyst composition wherein the novel feature is the method of preparing a catalyst from alumina phosphoric acid, ammonium hydroxide and water. Excellent results were obtained using a catalyst of this nature in batch-type reactions.

More recently, Vanderpool and co-workers in a series of U.S. patents (U.S. Pat. No. 4,540,822 issued Sept. 10, 1985; U.S. Pat. No. 4,578,518 and No. 4,578,519 issued Mar. 23, 1986; U.S. Pat. No. 4,584,406 issued Apr. 22, 1986 and U.S. Pat. No. 4,588,842 issued May 13, 1986) have disclosed that the reaction of monoethanolamine with ethylenediamine to provide essentially noncyclic polyethylenepolyamine reaction products can be effectively promoted with catalysts composed of a minor amount of phosphorus thermally, chemically bonded to a group IVb metal oxide support such as titania or zirconia. Also, in U.S. Pat. No. 4,555,582 issued Nov. 26, 1983 and U.S. Pat. No. 4,524,152 issued June 18, 1985, Vanderpool used a zirconium silicate catalyst to promote this reaction.

In addition, Vanderpool U.S. Pat. No. 4,540,822 issued Sept. 10, 1985 discloses a process for making essentially linear polyethylenepolyamines by reacting monoethanolamine with ethylenediamine in the presence of a catalyst composed of a minor amount of phosphorus thermally, chemically bonded to a group IVb metal oxide support wherein the catalyst is periodically regenerated. In Vanderpool et al. U.S. Pat. No. 4,609,761 which issued Sept. 2, 1986, a catalyst for this reaction is disclosed wherein a trialkyl phosphate or a trialkyl phosphite is initially deposited on titania as a source of phosphorus, and in Renken U.S. Pat. No. 4,612,397 which issued Sept. 16, 1986, a diammonium hydrogen phosphate is used as a source for the phosphorus in preparing the catalyst.

Zimmerschied et. al. U.S. Pat. No. 2,921,081 discloses catalysts for use in the conversion of olefins that are prepared by reacting a zirconium halide with a designated class of phosphoric acids.

Rylander et. al. U.S. Pat. No. 2,824,073 is concerned with the manufacture of a titanium-phosphoric acid catalyst that can be prepared by mixing titania with triphosphoric acid to form a doughy mixture which is thereafter dried and heated.

The text, "Refractories", by F. H. Norton (McGraw-Hill Book Company, Inc., 1949) in pages 318 and 319 discloses hafnium oxide, titanium oxide and zirconium oxides as well-known refractories.

SUMMARY OF THE INVENTION

Novel catalysts are disclosed which are prepared by reacting a minor amount of a phosphonitrillic chloride with titania to form an intermediate reaction product that is reacted with a diamine chelating agent such as ethylenediamine to provide a catalyst that can be used effectively to catalyze the reaction of monoethanolamine with ethylenediamine.

Thus, the catalysts are useful in the improved production of predominantly linear polyethylenepolyamines from ethylenediamine and monoethanolamine. The novel catalysts of the claimed invention can be prepared in a manner to be described from titania, a phosphonitrillic chloride, a diamine chelating agent and an acid scavenging agent.

DETAILED DESCRIPTION

Figure 1:
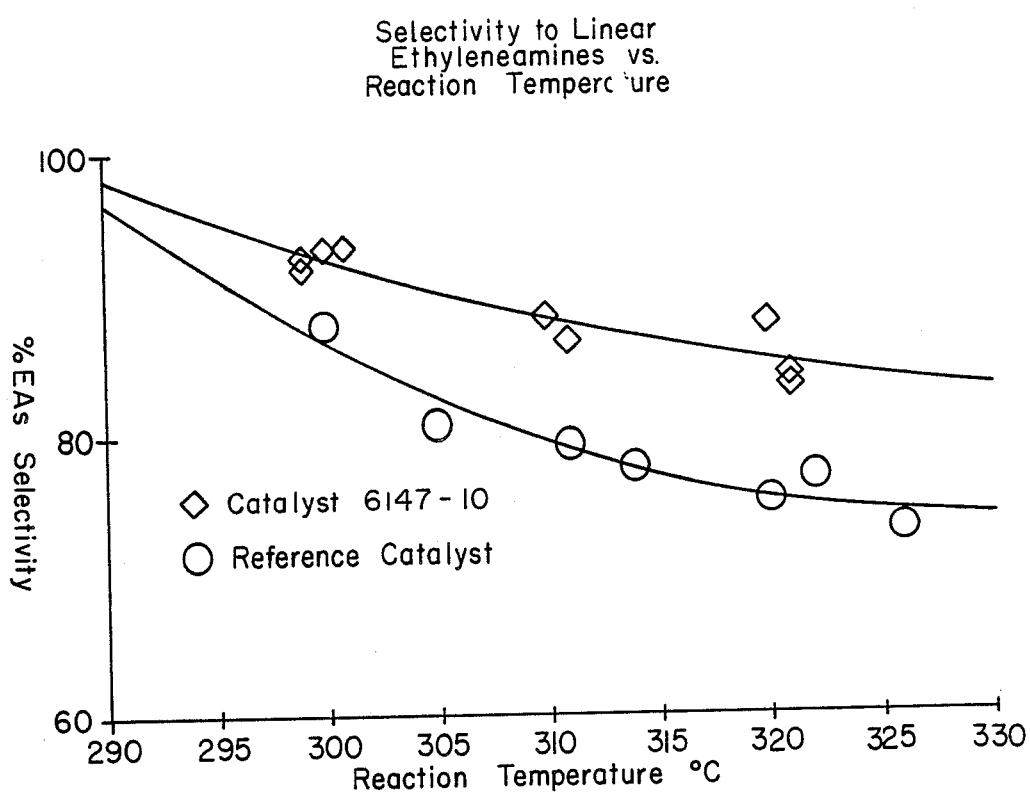
FIG. 1 is a graph illustrating the selectivity to linear ethyleneamines obtained with a catalyst of the present invention, in comparison with a reference catalyst, as a function of the reaction temperature.

In one aspect of the invention the catalysts of the present invention are used in producing essentially linear polyethylenepolyamines such as diethylenetriamine, triethylenetetramine, tetraethylenepentamine and pentaethylenehexamine from the reaction of ethylenediamine and monoethanolamine.

In another aspect, the present invention is directed to an improved catalyst composition derived from titania, phosphonitrillic chloride and ethylenediamine and to the method by which it is prepared.

PREPARATION OF POLYETHYLENEPOLYAMINES

The novel catalyst compositions catalyze the reaction of ethylenediamine with monoethanolamine at a temperature of from about 250° C. to about 400° C., preferably from about 270° C. to about 320° C. and a pressure of from about 500 (34.47 bar gauge) to about 3000 psig. (206.8 bar gauge) and preferably from about 1000 (68.9 bar gauge) to about 2000 psig. (137.8 bar gauge). Higher temperatures and pressures can be used, if desired, but there is no particular advantage in using such higher temperatures and/or pressures.

The pelleted catalyst compositions of the present invention are preferably employed as a fixed bed of catalyst in a continuous reaction system. In a continuous process of this nature, the time of contact of the reactants with the catalyst is one of the interrelated factors that those skilled in the art will adjust, along with temperature, pressure, bed geometry, pellet size, etc. in order to obtain a desired rate of reaction and, hence, a desired percentage of conversion of the reactants. Thus, in a continuous process, it is not necessary to drive the reaction to completion because unreacted feedstock components can be recycled to the reactor.

It is customary to use cylindrically-shaped catalyst pellets having a diameter essentially equal to the length thereof, such as diameters and lengths ranging from about 0.794 mm (1/32 inch) to about 9.525 mm (⅜ inch). It will be understood that the shape and dimensions of the pellets are not critical to the present invention and that pellets of any suitable shape and dimensions may be used as desired, by one wishing to practice the process of the present invention.

When cylindrical pellets of catalyst of the type described above are used, the weighted hourly space velocity may be varied within wide limits (e.g., 0.1 to 5 w/hr/w) in order to obtain a desired rate of conversion, as explained above. Normally, space velocities of about 0.5 to 2 w/hr/w will be employed.

Catalyst life is an important factor in conducting a continuous reaction. For example, if a catalyst is easily poisoned, or if catalyst pellets do not have good structural properties, the economics of the process will be seriously and adversely affected.

The catalysts of the present invention are not particularly susceptible to poisoning so this normally does not present a problem. However, under the reaction conditions employed, amines of the type used and formed herein have the potential capability of leaching or otherwise adversely affecting the structural integrity of the pellets. In an extreme instance, catalyst pellets having good initial crush strength and surface hardness will be reduced to fines very rapidly when used under reaction conditions such as those employed herein.

As a consequence, the catalyst compositions of the present invention are advantageously used for a continuous process for the continuous production of essentially linear polyethylenepolyamine reaction products from monoethanolamine and ethylenediamine. Such catalyst compositions can be used for prolonged periods without the need for regeneration (e.g., 1,000 hours or more). Nevertheless, with the passage of time deactivation will tend to slowly occur. Deactivation can be measured qualitatively as the increase of temperature required to maintain an essentially constant conversion rate for the monoethanolamine and ethylenediamine.

CATALYST PREPARATION

The catalyst compostions of the present invention are prepared from titania and a phosphonitrillic chloride using a diamine chelating agent and an acid scavenging agent. In the first step, titania pellets are immersed in an organic solvent solution of a phosphonitrillic chloride and an acid scavenging agent and heated at about 80° to about 150° C. for about 1 to about 24 hours to thereby at least partially react said phosphonitrillic chloride with a portion of said titania and to scavenge liberated chloride with said scavenging agent to form titania pellets containing an intermediate reaction product of said phosphonitrillic chloride with a portion of said titania. As a consequence, a binding of the phosphonitrillic chloride to the titania will occur. The exact nature of the reaction that occurs and the exact nature of the reaction product that is formed are not known.

Titania, a solid, normally inert material, is used as one of the starting materials of the present invention. It is preferably in the form of pre-formed high surface area pellets, such as pellets having a surface area of from about 2 to about 250M$^2$/gram. This is particularly desirable when the finished catalyst is to be used to catalyze a continuous process, such as one wherein monoethanolamine and ethylenediamine are continuously passed in liquid phase over a fixed bed of catalyst. However, if desired, the titania may be used in powdered form. This will be advantageous when the catalyst is to be used to catalyze a batch process. It is within the scope of the present invention to prepare the catalyst compositions using powdered titania as a starting material and to thereafter form the powdered catalyst into pellets using pelleting procedures known to those skilled in the art, such as procedures wherein the powdered titania is mixed with a minor amount of graphite and then compressed under pressure in a pellet-forming machine.

Titania is characterized as having the formula $TiO_2$. However, it is believed that hydroxyl groups are present on the surface of the titania and that, surprisingly, the hydroxyl groups will react with a phosphonitrillic chloride, at least to the extent that reaction products containing from about 0.1 to about 6 wt. % of phosphorus are formed. This is surprising because titania is essentially insoluble in water and organic solvents. However, organic solvent solutions of a phosphonitrillic chloride, and particularly aromatic solvent solutions apparently have the capacity to wet the surface of the titania at least to an extent to permit a limited reaction of the titania with the phosphonitrillic chloride. It is believed that the reaction may proceed as follows:

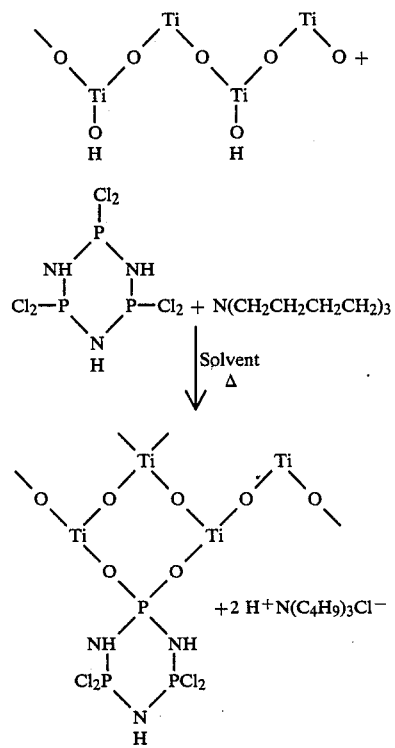

Any appropriate non-reactive organic solvent may be used, such as an aliphatic or an aromatic solvent such as benzene, toluene, xylenes, cyclohexane, n-heptane, pyridine, chloroform, diethyl ether, ethyl acetate, etc. The solvent should be one in which the phosphonitrillic chloride is soluble to an extent sufficient to permit the formation of an organic solvent solution containing from about 0.1 to about 50 wt. % of phosphonitrillic chloride.

Chloride is liberated during the course of the reaction forming one equivalent of hydrogen chloride for each P-Cl bond broken, so an acid scavenging agent which is soluble in the solvent and which will not form a precipitate should be used. Examples of suitable acid scavenging agents include hetero aromatic bases, trialkyl amines, etc. Representative of the trialkyl amines that may be used as acid scavenging agents are the $C_1$ to $C_8$ trialkyl amines such as trimethyl amine, tribuyl amine, trioctyl amine, etc. Representative examples of other acid scavenging agents that may be used include pyridine, lutidine, quinoline, etc.

In general, at least about 2 to about 25 wt. % phosphonitrillic chloride, based on the weight of the titania should be employed, and preferably, about 2 to about 10 wt. % of phosphonitrillic chloride, based on the weight of the titania. Larger quantities may be used, if desired, but there is no apparent adantage in doing so because the amount of phosphorus that will bind to the titania is limited. Thus, irrespective of the amount of the excess of the phosphonitrillic chloride that is employed, not more that about 6 wt. % of phosphorus will bind to the titania.

The amount of acid scavenging agent that is employed should be adequate to react, at least, with all of the hydrogen chloride that is liberated. Normally, from about 50 to about 300 wt. % of acid scavenging agent, based on the weight of the phosphonitrillic chloride will be adequate. In accordance with a preferred form of the present invention, from about 35 to about 200 wt. % of the acid scavenging agent will be used.

The reaction between the titania and the phosphonitrillic chloride will normally take place when the suspension of the titania in the solution is heated at a temperature of about 20° to about 150° C. More preferably, the temperature will be within the range of about 50° to about 110° C. The reaction time suitably may be within the range of about 1 to about 24 hours, and more preferably from about 1 to about 8 hours. There is no need to use an imposed pressure, so the reaction is preferably conducted at autogenous (atmospheric) pressure.

After the reaction between the titania and the phosphonitrillic chloride has been completed, the intermediate reaction product that is formed by the reaction should be recovered in any appropriate manner, such as for example, by decantation, draining, filtration, centrifugation, etc., and washed free of reaction by-products and unreacted acid scavenging agent and phosphonitrillic chloride.

The thus-recovered intermediate reaction product is then reacted with a diamine chelating agent to form the final catalyst composition of the present invention. Again, the solid intermediate product is immersed or otherwise suspended in an organic solvent solution of the reactants.

The amount of diamine chelating agent to be used should be an amount sufficient to react with all of the chlorine present in the intermediate reaction product of the titania with the phosphonitrillic chloride, and therefore is preferably used in molar excess. Thus, from about 1.1 to about 4 mole equivalents, based on the chloride originally present in the phosphonitrillic chloride, should be used, and more preferably, from about 1.2 to about 2 mole equivalents of diamine chelating agent per mole equivalent of chloride originally present in the phosphonitrillic chloride should be used.

The diamine chelating agent is dissolved in a suitable organic solvent, such as a solvent of the type described above. The amount of solvent to be used suitably will be sufficient to form about a 0.1 to 100 wt. % solution of the ethylenediamine in the solvent, and more preferably, about a 10 to about a 50 wt. % solution. An acid scavenging agent will also be present, and may be the same or different from the acid scavenging agent used during the reaction of the titania with the phosphonitrillic chloride. Again, a molar excess of acid scavenging agent should be present, so the amount of acid scavenging agent to be used should be at least a two molar amount, based on the diamine chelating agent, and more preferably will comprise from about 2 to about 4 moles of acid scavenging agent per mole of diamine chelating agent.

The reaction conditions to be employed in the second reaction step are suitable within the same ranges specified for the first reaction step (i.e., a reaction at atmospheric pressure at a temperature within the range of about 20° to about 150° C., such as about 50° to about 110° C., and a reaction time within the range of about 1 to about 24 hours, such as about 1 to about 8 hours to thereby, e.g., at least partially react said ethylene diamine with said intermediate reaction product to form a final pelleted reaction product).

The exact composition of the final reaction product that is formed as a result of the reaction of the ethylenediamine with the second reaction product is not known. However, it is believed that the ethylenediamine reacts with the residual chlorine present in the intermediate reaction product in the following manner:

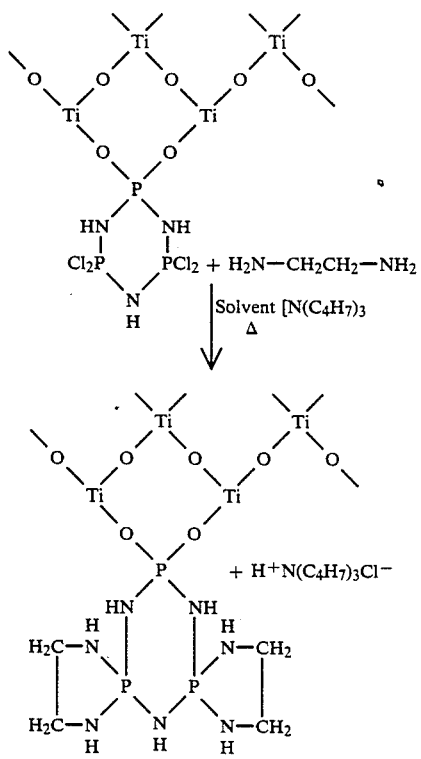

At the end of the second reaction step the final reaction product is separated and recovered from the organic solvent solution in any appropriate manner, such as by draining, decantation, filtration, centrifugation, etc., and is then washed with solvent (e.g., toluene) and dried.

The pelleted catalyst compositions of the present invention should be calcined. They can be calcined prior to use or calcined in situ when used as catalysts at temperatures in excess of about 100° C. When the catalysts are to be calcined prior to use, calcination is suitably conducted for 2 to 24 hours such as about 1 to about 8 hours at a temperature of at least 100° C. but below the temperature at which thermal alteration of the catalyst occurs. This can be determined by routine experimentation for a particular catalyst. Temperatures above about 500° C. should be avoided. A suitable calcining temperature range is normally about 200° to about 500° C. and, more preferably, 300° to 400° C.

In any event, in-situ calcining will occur when the pelleted compositions are used to catalyze the reaction of monoethanolamine with ethylenediamine at 250° to 400° C.

There are many compounds which can be formed from the reaction of ethylenediamine and monoethanolamine besides the preferred linear polyethylenepolyamines such as diethylenetriamine, triethylenetetramine, tetraethylenepentamine and pentaethylenehexamine. Less desirable cyclics and other compounds, such as piperazine, N-(2-aminoethyl)ethanolamine and N-(2-aminoethyl)piperazine, are also formed. The more desired linear polyethylenepolyamines can be easily recovered from the reaction product mixture by conventional methods such as distillation. Such distillation recovery methods are well known in the art. An outstanding advantage of the claimed invention is that the lower molecular weight polyethylenepolyamines recovered from the reaction mixture can be further reacted with monoethanolamine to produce a larger percentage of the higher molecular weight linear polyethylenepolyamines.

The following examples will further illustrate the preparation of predominantly linear polyethylenepolyamines from ethylenediamine and monoethanolamine by the use of the catalyst compositions of the present invention. They are given by way of illustration and not as limitations on the scope of the invention. Thus, it will be understood that reactants, proportions of reactants, and time, temperature and pressure of the reaction steps may be varied with much the same results achieved.

For purposes of convenience and brevity, the reactant compounds employed and the products obtained have been abbreviated in the following examples and tables. The abbreviations employed for these various compounds are:

EDA—ethylenediamine
MEA—monoethanolamine
PIP—piperazine
DETA—diethylenetriamine
TETA—triethylenetetramine
TEPA—tetraethylenepentamine
AEEA—N-(2-aminoethyl)ethanolamine
AEP—N-(2-aminoethyl)piperazine
HEP—N-(hydroxyethyl)piperazine
DIAEP—diaminoethylpiperazine
PEEDA—piperazineoethyl-ethylenediamine
AETETA—aminoethyltriethylene tetramine.

WORKING EXAMPLES

The present invention will be further illustrated by the following working examples.

I. Catalyst Preparation (6147-10)

A preformed pelleted titanium dioxide catalyst support (225 g, 220 cc) was placed in a roundbottom flask. A solution of phosphonitrillic chloride (11.5 g) and tributyl amine (20.1 g) in 95 cc of dry toluene was added. The mixture was heated in an oil bath at 100° C. for 4 hours then cooled and rinsed three times with dry toluene. The drained carrier was then treated with a solution of ethylenediamine (7.2 g) and tributyl amine (45.8 g) in 100 cc of dry toluene, heated and rinsed as before. The catalyst was then dried for 1 hr at 150° C. and calcined 2 hr at 350° C. It contained 1.3% P by AA (atomic absorption analysis).

II. Use as a Catalyst for Formation of Ethyleneamines (6147-12)

The above catalyst was placed in a stainless steel tube in an aluminum heating block (100 cc of catalyst). Through the tube was passed a mixture of EDA (2 pbw) and MEA (1 pbw) at a rate of 100 cc per hour. The apparatus was held at a series of temperatures 3 to 4 hours to allow equilibration and samples were taken for analysis by GLC. The area % analysis along with the calculated % MEA conversion, % EDA conversion, DETA/Piperazine ratio, and percent non-cyclic products in the TETA range as well as the relevant selectivities among the observed products is presented for each of the samples in Table I-A, Table I-B and Table I-C.

TABLE I-A

Ethyleneamines Continuous Reactor Products
Cyclic Phosphamine on Titania
Catalyst 6147-10

| 1 Sample | 2 Temp. °C. | 3 Area % EDA | 4 Area % MEA | 5 % MEA Conv. | 6 Area % PIP | 7 % Selec. to PIP | 8 Area % BAEE | 9 % Selec. to BAEE | 10 % Conv. of EDA | 11 Area % DETA | 12 % Selec. to DETA |
|---|---|---|---|---|---|---|---|---|---|---|---|
| Feed |  | 65.23 | 34.76 |  |  |  |  |  |  |  |  |
| 6147-12-1 | 300 | 56.58 | 17.75 | 48.92 | 0.22 | 1.08 | 0.00 | 0.00 | 13.26 | 17.74 | 86.91 |
| 6147-12-2 | 299 | 59.36 | 20.59 | 40.76 | 0.20 | 1.20 | 0.00 | 0.00 | 9.00 | 17.07 | 87.49 |
| 6147-12-3 | 306 | 57.73 | 17.97 | 48.30 | 0.40 | 1.72 | 0.00 | 0.00 | 11.50 | 19.22 | 81.29 |
| 6147-12-4 | 280 | 62.09 | 27.15 | 21.88 | 0.03 | 0.35 | 0.00 | 0.00 | 4.82 | 10.35 | 96.57 |
| 6147-12-5 | 281 | 64.30 | 24.95 | 28.20 | 0.14 | 1.37 | 0.00 | 0.00 | 1.43 | 10.07 | 94.28 |
| 6147-12-6 | 290 | 61.90 | 22.74 | 34.56 | 0.23 | 1.51 | 0.00 | 0.00 | 5.11 | 13.54 | 89.30 |
| 6147-12-7 | 290 | 61.62 | 23.54 | 32.26 | 0.21 | 1.43 | 0.00 | 0.00 | 5.54 | 13.09 | 89.33 |
| 6147-12-8 | 299 | 59.18 | 20.30 | 41.59 | 0.35 | 1.76 | 0.00 | 0.00 | 9.28 | 16.66 | 83.78 |
| 6148-12-9 | 300 | 59.85 | 19.37 | 44.26 | 0.35 | 1.73 | 0.00 | 0.00 | 8.25 | 16.64 | 82.27 |
| 6147-12-10 | 311 | 55.17 | 14.22 | 59.07 | 0.63 | 2.16 | 0.02 | 0.09 | 15.42 | 21.58 | 73.99 |
| 6147-12-11 | 310 | 56.12 | 14.04 | 59.60 | 0.60 | 2.12 | 0.02 | 0.08 | 13.96 | 21.49 | 75.28 |
| 6147-12-12 | 320 | 55.23 | 13.34 | 61.62 | 0.76 | 2.49 | 0.06 | 0.20 | 15.33 | 21.77 | 70.89 |
| 6147-12-13 | 321 | 55.99 | 3.44 | 90.09 | 1.08 | 2.92 | 0.04 | 0.12 | 14.16 | 25.25 | 67.97 |
| 6147-12-14 | 321 | 55.90 | 3.76 | 89.18 | 1.03 | 2.83 | 0.04 | 0.12 | 14.30 | 24.77 | 67.71 |
| 6147-12-15 | 299 | 60.37 | 19.01 | 45.30 | 0.33 | 1.69 | 0.00 | 0.00 | 7.44 | 16.96 | 85.75 |
| 6147-12-16 | 301 | 56.58 | 22.24 | 36.00 | 0.22 | 1.08 | 0.00 | 0.00 | 13.26 | 17.74 | 86.91 |

TABLE I-B

| 1 Sample | 13 Area % AEEA | 14 % Selec. to AEEA | 15 Ratio: Obsv. DETA/ Obsv. PIP | 16 Area % of AEP | 17 % Selec. of AEP | 18 Area % NTEA | 19 % Selec. to NTEA | 20 % of NC | 21 Area % to TETA | 22 % Selec. of TETA |
|---|---|---|---|---|---|---|---|---|---|---|
| 6147-12-1 | 0.21 | 1.07 | 80.27 | 0.23 | 1.13 | 0.18 | 0.89 | 100.00 | 1.81 | 8.90 |
| 6147-12-2 | 0.28 | 1.45 | 72.64 | 0.19 | 1.01 | 0.17 | 0.88 | 100.00 | 1.54 | 7.93 |
| 6147-12-3 | 0.24 | 1.04 | 47.35 | 0.24 | 1.05 | 0.28 | 1.22 | 99.24 | 3.16 | 13.39 |
| 6147-12-4 | 0.17 | 1.70 | 279.75 | 0.04 | 0.36 | 0.01 | 0.13 | 36.36 | 0.03 | 0.25 |
| 6147-12-5 | 0.18 | 1.70 | 69.00 | 0.03 | 0.35 | 0.01 | 0.13 | 19.18 | 0.03 | 0.31 |
| 6147-12-6 | 0.32 | 2.15 | 58.87 | 0.09 | 0.62 | 0.08 | 0.56 | 100.00 | 0.88 | 5.83 |
| 6147-12-7 | 0.35 | 2.44 | 62.04 | 0.09 | 0.64 | 0.08 | 0.59 | 100.00 | 0.81 | 5.54 |
| 6147-12-8 | 0.35 | 1.77 | 47.47 | 0.18 | 0.93 | 0.21 | 1.06 | 100.00 | 2.12 | 10.68 |
| 6147-12-9 | 0.34 | 1.69 | 47.29 | 0.18 | 0.90 | 0.20 | 0.99 | 100.00 | 2.49 | 12.32 |
| 6147-12-10 | 0.27 | 0.96 | 34.21 | 0.47 | 1.63 | 0.47 | 1.61 | 89.75 | 4.62 | 15.82 |
| 6147-12-11 | 0.23 | 0.81 | 35.47 | 0.45 | 1.58 | 0.43 | 1.51 | 87.77 | 4.32 | 15.13 |
| 6147-12-12 | 0.08 | 0.28 | 28.38 | 1.00 | 3.25 | 0.45 | 1.47 | 86.25 | 5.11 | 16.65 |
| 6147-12-13 | 0.12 | 0.33 | 23.25 | 1.05 | 2.83 | 0.64 | 1.73 | 96.11 | 7.40 | 19.93 |
| 6147-12-14 | 0.12 | 0.33 | 23.91 | 1.02 | 2.79 | 0.64 | 1.75 | 96.46 | 7.32 | 20.02 |
| 6147-12-15 | 0.31 | 1.59 | 50.49 | 0.20 | 1.05 | 0.17 | 0.86 | 100.00 | 1.78 | 9.02 |
| 6147-12-16 | 0.21 | 1.07 | 80.27 | 0.23 | 1.13 | 0.18 | 0.89 | 100.00 | 1.81 | 8.90 |

TABLE I-C

| 1 Sample | 23 Area % of DIAEP | 24 % Selec. of DIAEP | 25 Area % of PEEDA | 26 % Selec. of PEEDA | 27 Area % of AETETA | 28 % Selec. to AETETA | 29 Area % of TEPA | 30 % Selec. of TEPA | 31 Total Product |
|---|---|---|---|---|---|---|---|---|---|
| 6147-12-1 | 0.00 | 0.00 | 0.00 | 0.00 | 0.00 | 0.00 | 0.00 | 0.00 | 20.41 |
| 6147-12-2 | 0.00 | 0.00 | 0.00 | 0.00 | 0.00 | 0.00 | 0.00 | 0.00 | 19.51 |
| 6147-12-3 | 0.02 | 0.09 | 0.00 | 0.00 | 0.00 | 0.00 | 0.05 | 0.19 | 23.67 |
| 6147-12-4 | 0.07 | 0.65 | 0.00 | 0.00 | 0.00 | 0.00 | 0.00 | 0.00 | 10.72 |
| 6147-12-5 | 0.19 | 1.85 | 0.00 | 0.00 | 0.00 | 0.00 | 0.00 | 0.00 | 10.69 |
| 6147-12-6 | 0.00 | 0.00 | 0.00 | 0.00 | 0.00 | 0.00 | 0.00 | 0.00 | 15.16 |
| 6147-12-7 | 0.00 | 0.00 | 0.00 | 0.00 | 0.00 | 0.00 | 0.00 | 0.00 | 14.65 |
| 6147-12-8 | 0.00 | 0.00 | 0.00 | 0.00 | 0.00 | 0.00 | 0.00 | 0.00 | 19.89 |
| 6147-12-9 | 0.00 | 0.00 | 0.00 | 0.00 | 0.00 | 0.00 | 0.01 | 0.06 | 20.23 |
| 6147-12-10 | 0.39 | 1.34 | 0.18 | 0.65 | 0.23 | 0.80 | 0.27 | 0.95 | 29.18 |
| 6147-12-11 | 0.43 | 1.52 | 0.22 | 0.79 | 0.18 | 0.65 | 0.13 | 0.48 | 28.55 |
| 6147-12-12 | 0.57 | 1.86 | 0.31 | 1.01 | 0.25 | 0.84 | 0.30 | 1.00 | 30.70 |
| 6147-12-13 | 0.17 | 0.46 | 0.15 | 0.41 | 0.41 | 1.12 | 0.79 | 2.15 | 37.15 |
| 6147-12-14 | 0.14 | 0.39 | 0.14 | 0.40 | 0.42 | 1.16 | 0.89 | 2.44 | 36.58 |
| 6147-12-15 | 0.00 | 0.00 | 0.00 | 0.00 | 0.00 | 0.00 | 0.00 | 0.00 | 19.78 |

TABLE I-C-continued

| Sample | 23 Area % of DIAEP | 24 % Selec. of DIAEP | 25 Area % of PEEDA | 26 % Selec. of PEEDA | 27 Area % of AETETA | 28 % Selec. to AETETA | 29 Area % of TEPA | 30 % Selec. of TEPA | 31 Total Product |
|---|---|---|---|---|---|---|---|---|---|
| 6147-12-16 | 0.00 | 0.00 | 0.00 | 0.00 | 0.00 | 0.00 | 0.00 | 0.00 | 20.41 |

III. Use of Reference Catalyst to Prepare Ethyleneamines

In order to provide a comparison of the improvement in catalyst activity that is obtainable with the catalysts of the present invention, a reference catalyst was also used to catalyze the reaction of ethylenediamine with monoethanolamine in the manner and in the equipment described above in Example II. The reference catalyst was a titania-supported phosphorus catalyst prepared by immersing titania pellets in concentrated phosphoric acid, after which the immersed titania was drained of excess liquid and then calcined. The reference catalyst had been used for extensive pilot plant studies of the process under consideration and had been found to be the most consistantly active catalyst of all of the catalysts that were tested.

The results of this series of test were was follows:

TABLE II

Selectivity to Linear Polyethylenepolyamines
Reference Catalyst

| Temp. °C. | % MEA Conv. | % of Linear Polyethylene-polyamines |
|---|---|---|
| 300 | 38.3 | 87.8 |
| 305 | 45.9 | 80.7 |
| 311 | 59.4 | 79.4 |
| 314 | 64.3 | 77.8 |
| 320 | 65.9 | 75.4 |
| 322 | 73.2 | 77.0 |
| 326 | 99.9 | 73.2 |

TABLE III

Selectivity to Linear Polyethylenepolyamines
Catalyst 6147-10
of the Present Invention

| Temp. °C. | % MEA Conv. | % of Linear Polyethylene-polyamines |
|---|---|---|
| 299 | 41.6 | 92.6 |
| 299 | 45.3 | 91.8 |
| 300 | 44.3 | 93.2 |
| 301 | 36.0 | 93.3 |
| 310 | 59.6 | 88.4 |
| 311 | 59.1 | 86.6 |
| 320 | 61.6 | 87.9 |
| 321 | 90.1 | 84.1 |
| 321 | 89.2 | 83.4 |

Figure 2:
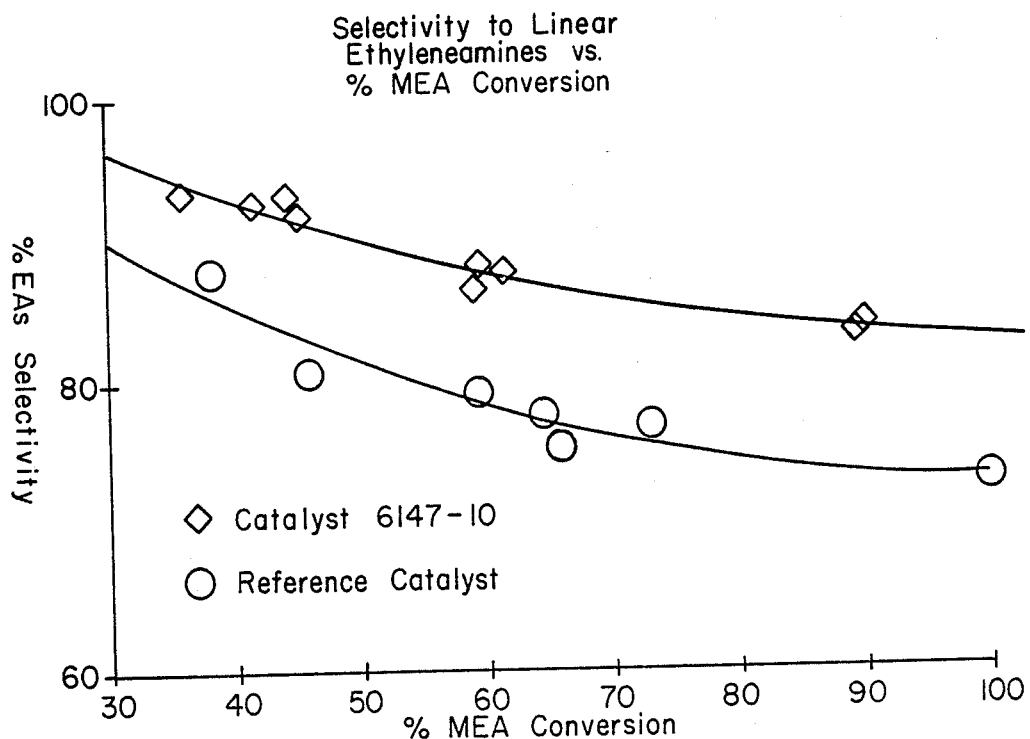
FIG. 2 is a graph illustrating the selectivity to linear ethyleneamines obtained with a catalyst of the present invention, in comparison with a reference catalyst, as a function of the percent of conversion of monoethanolamine.

Turning now to the drawings and especially to FIG. 2, where the data from Tables II and III has been plotted to show the selectivity to linear amines obtained with the catalyst of the present invention, as compared with the reference catalyst, it will be noted that an almost constant 10% increase in selectivity to linear ethyleneamines was obtained with the catalyst of the present invention. This result was surprising and unexpected, because the reference catalyst was the most effective catalyst known to the inventors prior to their discovery of the catalyst compositions of the present invention. Also, it is surprising that the enhanced selectivity was obtained over such a wide range of monoethanolamine conversion.

Turning now to FIG. 1, wherein the selectivity to linear ethyleneamines is plotted relative to reaction temperature, it will be noted that the catalyst composition of the present invention again demonstrated surprising and unexpected results. Although the catalyst of the present invention was only slightly superior to the reference catalyst at the lower end of the temperature range, the superiority became more pronounced as the temperature was increased, amounting to about a 10% increase in selectivity at a reaction temperature of about 330° C.

The foregoing examples have been given by way of illustration and not as limitations on the scope of this invention, as defined by the appended claims.

I claim:

1. A new composition of matter prepared by treating titania with a solvent solution of phosphonitrillic chloride and an acid scavenging agent under conditions to form titania containing an intermediate reaction product of said phosphonitrillic chloride with a portion of said titania, next treating said intermediate reaction product with a solvent solution of a diamine chelating agent and an acid scavenging agent under conditions to form a final reaction product, and calcining said final reaction product to catalytically activate said final reaction product, said solvent solution of said phosphonitrillic chloride containing about 2 to about 25 wt. % of said phosphonitrillic chloride, based on the weight of the titania and a molar excess of said acid scavenging agent, based on the moles of chloride in said phosphonitrillic chloride, and said solvent solution of said diamine chelating agent containing about 1.1 to about 4 mole equivalents of diamine chelating agent per mole equivalent of chloride originally present in said phosphonitrillic acid and a molar excess of said acid scavenging agent, based on the moles of chloride originally present in said phosphonitrillic chloride.

2. A new composition of matter prepared by the process comprising the steps of:

treating titania with a solvent solution of phosphonitrillic chloride and an acid scavenging agent at a temperature within the range of about 20° to about 150° C. for about 1 to about 24 hours to thereby form titania containing an intermediate reaction product of said phosphonitrillic chloride with a portion of said titania, said solvent solution of said phosphonitrillic chloride containing about 2 to about 25 wt. % of said phosphonitrillic chloride, based on the weight of the titania and a molar excess of said acid scavenging agent, based on the moles of chloride in said phosphonitrillic chloride, recovering said intermediate reaction product, treating said intermediate reaction product with a solvent solution of a diamine chelating agent and an acid scavenging agent at a temperature within the range of about 20° to about 150° C. for about 1 to about 24 hours to thereby provide a final reaction product, and recovering said final reaction product and calcining said final reaction product at a temperature within the range of about 200° to about 500° C. for about 1 to about 8 hours to thereby catalytically activate said final reaction product, said solvent solution of said diamine chelating agent containing about 1.1 to about 4 mole equivalents of diamine chelating agent per mole equivalent of chloride originally present in said phosphonitrillic chloride and a molar excess of said acid scavenging agent, based on the moles of chloride originally present in said phosphonitrillic chloride.

3. A new composition of matter prepared by the process comprising the steps of:

maintaining titania pellets immersed in a solvent solution of phosphonitrillic chloride and an acid scavenging agent at a temperature within the range of about 20° to about 150° C. for about 1 to about 24 hours to thereby at least partially react said phosphonitrillic acid with said titania and to scavange liberated chloride from said reaction mixture by reaction of said chloride with said scavenging agent to form titania pellets containing an intermediate reaction product of said phosphonitrillic chloride with titania, said solvent solution of said phosphonitrillic chloride containing about 2 to about 25 wt. % of said phosphonitrillic chloride, based on the weight of the titania and a molar excess of said acid scavenging agent, based on the moles of chloride in said phosphonitrillic chloride, recovering said pelleted intermediate reaction product, maintaining said pelleted intermediate reaction product immersed in a solvent solution of a diamine chelating agent and an acid scavenging agent at a temperature within the range of about 20° to about 150° C. for about 1 to about 24 hours to react said diamine chelating agent with said intermediate reaction product to thereby provide a final pelleted reaction product, and recovering said final reacton product and calcining said final reacton product at a temperature within the range of about 200° to about 500° C. for about 1 to about 8 hours to thereby catalytically activate said final reaction product, said solvent solution of said diamine chelating agent containing about 1.1 to about 4 mole equivalents of diamine chelating agent per mole equivalent of chloride originally present in said phosphonitrillic chloride and a molar excess of said acid scavenging agent, based on the moles of chloride originally present in said phosphonitrillic chloride.

4. A composition as in claim 3 prepared by reacting said titania pellets with about 2 to about 10 wt. % of phosphonitrillic chloride, based on the weight of the titania.

5. A composition as in claim 4 wherein the phosphonitrillic chloride is reacted with the titania pellets and the diamine chelating agent is reacted with the intermediate reaction product at autogenous pressure at a temperature of about 50° to about 110° C. for about 1 to about 8 hours.

6. A new catalytically active composition of matter prepared by the process comprising the steps of:

immersing titania pellets in an organic aromatic solvent solution of phosphonitrillic chloride and an acid scavenging agent, said aromatic organic solvent solution containing about 2 to about 10 wt. % of said phosphonitrillic chloride, based on the weight of the titania, and a molar excess of said acid scavenging agent, based on the moles of chlorine in said phosphonitrillic chloride, maintaining said titania pellets immersed in said organic solvent solution of phosphonitrillic acid at a temperature within the range of about 50° to about 110° C. for about 1 to about 8 hours to thereby react a portion of the titania with said phosphonitrillic chloride to form titania pellets containing an intermediate reaction product of said phosphonitrillic chloride with titania, recovering said pelleted intermediate reaction product, immersing said intermediate reaction product in a second aromatic solvent solution of a diamine chelating agent and an acid scavenging agent, said second aromatic solvent solution containing about 1.1 to about 2 mole equivalents of said diamine chelating agent based on the chloride originally present in said phosphonitrillic chloride in said first organic aromatic solvent solution and a molar excess of said acid scavenging agent, based on the moles of chloride in said phosphonitrillic chloride, maintaining said pelleted intermediate reaction product immersed in said second solvent solution at a temperature within the range of about 50° to about 110° C. for about 1 to about 8 hours to thereby at least partially react said ethylene diamine with said intermediate reaction product to form a final pelleted reaction product, and recovering and calcining said final reaction product at a temperature within the range of about 200° to about 500° C. for about 1 to about 8 hours to thereby catalytically activate said final reaction product.

7. A composition as in claim 6 wherein the acid scavenging agent is a $C_1$ to $C_8$ trialkyl amine and the diamine chelating agent is ethylene diamine.

8. A composition as in claim 7 wherein the trialkyl amine is tributyl amine.

9. A method for making a new composition of matter which comprises the steps of:

maintaining titania pellets immersed in a solvent solution of phosphonitrillic chloride and an acid scavenging agent at a temperature within the range of about 20° to about 150° C. for about 1 to about 24 hours to thereby at least partially react said phosphonitrillic acid with said titania and to scavange liberated chloride from said reaction mixture by reaction of said chloride with said scavenging agent to form titania pellets containing an intermediate reaction product of said phosphonitrillic chloride with titania, said solvent solution containing about 2 to about 25 wt. % of phosphonitrillic chloride, based on the weight of the titania and from about 50 to about 300 wt. % of said acid scavenging agent, based on the weight of the phosphonitrillic chloride, recovering said pelleted intermediate reaction product, maintaining said pelleted intermediate reaction product immersed in a solvent solution of a diamine chelating agent and an acid scavenging agent at a temperature within the range of about 20° to about 150° C. for about 1 to about 24 hours to react said diamine chelating agent with said intermediate reaction product to thereby provide a final pelleted reaction product, and recovering said final reaction product and calcining said final reaction product at a temperature within the range of about 200° to about 500° C. for about 1 to about 8 hours to thereby catalytically activate said final reaction product, said solvent solution of said diamine chelating agent containing about 1.1 to about 4 mole equivalents of diamine chelating agent per mole equivalent of chloride originally present in said phosphonitrillic chloride and from about 2 to about 4 moles of said acid scavenging agent per mole of said diamine chelating agent.

10. A method as in claim 9 wherein said titania pellets are reacted with about 2 to about 10 wt. % of phosphonitrillic chloride, based on the weight of the titania.

11. A method as in claim 10 wherein the phosphonitrillic chloride is reacted with the titania pellets and the diamine chelating agent is reacted with the intermediate reaction product at autogenous pressure at a temperature of about 50° to about 110° C. for about 1 to about 8 hours.

12. A method for preparing a new catalytically active composition of matter prepared comprising the steps of:

immersing titania pellets in an organic aromatic solvent solution of phosphonitrillic chloride and an acid scavenging agent, said aromatic organic solvent solution containing about 2 to about 10 wt. % of said phosphonitrillic chloride, based on the weight of the titania, and a molar excess of said acid scavenging agent, based on the moles of chlorine in said phosphonitrillic chloride, maintaining said titania pellets immersed in said organic solvent solution of phosphonitrillic acid at a temperature within the range of about 50° to about 110° C. for about 1 to about 8 hours to thereby react a portion of the titania with said phosphonitrillic chloride to form titania pellets containing an intermediate reaction product of said phosphonitrillic chloride with titania, recovering said pelleted intermediate reaction product, immersing said intermediate reaction product in a second aromatic solvent solution of a diamine chelating agent and an acid scavenging agent, said second aromatic solvent solution containing about 1.1 to about 2 mole equivalents of said diamine chelating agent based on the chloride originally present in said phosphonitrillic chloride in said first organic aromatic solvent solution and a molar excess of said acid scavenging agent, based on the moles of chloride in said phosphonitrillic chloride, maintaining said pelleted intermediate reaction product immersed in said second solvent solution at a temperature within the range of about 50° to about 110° C. for about 1 to about 8 hours to thereby at least partially react said ethylene diamine with said intermediate reaction product to form a final pelleted reaction product, and recovering and calcining said final reaction product at a temperature within the range of about 200° to about 500° C. for about 1 to about 8 hours to thereby catalytically activate said final reaction product.

13. A method as in claim 12 wherein the acid scavenging agent is a $C_1$ to $C_8$ trialkyl amine and the diamine chelating agent is ethylene diamine.

14. A method as in claim 13 wherein the trialkyl amine is tributyl amine.

15. A method for preparing a catalytically active composition of matter which comprises the steps of:

treating titania with a solvent solution of phosphonitrillic chloride and an acid scavenging agent at a temperature within the range of about 20° to about 150° C. for about 1 to about 24 hours to thereby form titania containing an intermediate reaction product of said phosphonitrillic chloride with a portion of said titania, said solvent solution of said phosphonitrillic chloride containing about 2 to about 25 wt. % of said phosphonitrillic chloride, based on the weight of the titania and a molar excess of said acid scavenging agent, based on the moles of chloride in said phosphonitrillic chloride, recovering said intermediate reaction product, treating said intermediate reaction product with a solvent solution of a diamine chelating agent and an acid scavenging agent at a temperature within the range of about 20° to about 150° C. for about 1 to about 24 hours to thereby provide a final reaction product, and recovering said final reaction product and calcining said final reaction product at a temperature within the range of about 200° to about 500° C. for about 1 to about 8 hours to thereby catalytically activate said final reaction product, said solvent solution of said diamine chelating agent containing about 1.1 to about 4 mole equivalents of diamine chelating agent per mole equivalent of chloride originally present in said phosphonitrillic chloride and a molar excess of said acid scavenging agent, based on the moles of chloride originally present in said phosphonitrillic chloride.

* * * * *